United States Patent [19]

Neeb et al.

[11] Patent Number: 4,831,168

[45] Date of Patent: May 16, 1989

[54] PROCESS FOR PREPARING 2-HYDROXYDIBENZOFURAN-3-CARBOXYLIC ACID AND ALKALI METAL SALTS THEREOF

[75] Inventors: Rudolf Neeb, Offenbach am Main; Wolfgang Ironich, Eppstein/Taunus, both of Fed. Rep. of Germany

[73] Assignee: Hoechst Aktiengesellschaft, Frankfurt am Main, Fed. Rep. of Germany

[21] Appl. No.: 142,333

[22] Filed: Dec. 29, 1987

Related U.S. Application Data

[63] Continuation of Ser. No. 858,355, May 1, 1986, abandoned.

[30] Foreign Application Priority Data

May 3, 1985 [DE] Fed. Rep. of Germany ....... 3515873

[51] Int. Cl.$^4$ ............................................. C07D 302/91
[52] U.S. Cl. ................................................... 549/461
[58] Field of Search ........................ 549/461; 562/424

[56] References Cited

U.S. PATENT DOCUMENTS 2,050,958  8/1936  Muth ................................... 549/461
2,453,105  11/1948  Wolthuis et al. .
2,646,355  7/1953  Zweitel et al. .
2,824,892  2/1958  Barkley ............................... 562/424
3,655,697  4/1972  Shen et al. .......................... 549/461

FOREIGN PATENT DOCUMENTS 593506  2/1934  Fed. Rep. of Germany ...... 549/461

OTHER PUBLICATIONS

BIOS Final Report No. 1149, pp. 93–94.
M. R. R. Bhagwanth et al., *Chem. Abs.* 72:44997w (1970).
P. Madhavan Nair, et al., *Chem. Abs.* 55:7339i to 7341e (1961).
K. Teranishi et al. (Mitsui Petrochem. Ind. Ltd.), *Chem. Abs.* 85:49737q (1976) (=JP 75-1099).
M. Kamel et al., *Chem. Abs.* 80:95662f (1974).
Roempps Chemie-Lexikon, 8th Ed., vol. I, ed. Neumueller, Frankh'sche Verlagshandlg., Stuttgart, 1979, p. 540.
Houben–Weyl *Methoden der Organischen Chemie*, 4th Ed., vol. VIII, ed. E. Mueller, Georg Thieme Verlag, Stuttgart, 1952, pp. 372–373.

*Primary Examiner*—Mary C. Lee
*Assistant Examiner*—Bernard I. Dentz

[57] ABSTRACT

2-Hydroxydibenzofuran-3-carboxylic acid and its alkali metal salts are prepared by reacting an alkali metal salt of 2-hydroxydibenzofuran with carbon dioxide, where appropriate under pressure, at a temperature above 120° C. in an aliphatic alcohol of 4 to 8 carbon atoms.

21 Claims, No Drawings

PROCESS FOR PREPARING 2-HYDROXYDIBENZOFURAN-3-CARBOXYLIC ACID AND ALKALI METAL SALTS THEREOF

The invention relates to the technical field of the synthesis of intermediates which are preferably used in the preparation of dyes.

2-hydroxydibenzofuran-3-carboxylic acid of the formula

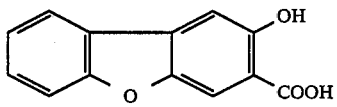

is in particular in the form of its arylamides an intermediate for the preparation of water-insoluble azo dyes (see for example German Reich Pat. No. 607,381, reprinted in Friedländer, Fortschritte der Teerfarbenfabrikation, 21,275, and Colour Index C.I. No. 37,605). It is prepared by carboxylating the alkali metal salts of 2-hydroxydibenzofuran using the Kolbe-Schmitt reaction (see German Reich Pat. No. 593,506, reprinted in Friedländer 20, 487). A detailed procedure for this carboxylation reaction is described in BIOS Final Report No. 1149, page 93. Therein 2-hydroxydibenzofuran (referred to in BIOS as 3-hydroxydiphenylene oxide) is carboxylated in the form of its dry sodium salt at a temperature of 260° to 265° C. under carbon dioxide pressure of about 4.5 bar for about 20 hours, and the reaction batch needs to be interrupted after about 10 hours to allow the degree of conversion to be checked. The dry sodium salt of 2-hydroxydibenzofuran, which serves as the starting compound, needs to be prepared deforehand in a complicated manner by heating 2-hydroxydibenzofuran with aqueous sodium hydroxide solution at 145° to 150° C. for 6 hours and subsequently concentrating the resulting paste under reduced pressure at a temperature up to 225° C. in the course of 8 hours. The carboxylation mixture is worked up after completion of the carboxylation reaction by splitting this batch into four separate batches. Each portion is then dissolved in 66 times the weight of water, to which a little bisulfite liquor has been added. The solution is first brought with sulfuric acid to weakly acid pH and then with sodium carbonate to an exactly neutral pH; after clarification of the solution the 2-hydroxydibenzofuran-3-carboxylic acid is precipitated therefrom with a little excess sulfuric acid and is obtained in a yield of 84% of theory. The acid is still contaminated with free 2-hydroxydibenzofuran. If the free 2-hydroxydibenzofuran content in the acid is 2 to 4% by weight and higher, it needs to be removed for reasons of quality from the 2-hydroxydibenzofuran-3-carboxylic acid by an expensive sublimation process.

It is obvious that this known process has several serious shortcomings which by present day standards are not conducive to economical manufacture of this product. For instance, in particular the long dehydration phase to prepare the dry sodium salt of 2-hydroxydibenzofuran, the long carboxylation phase and in particular the large volume required for dissolving the carboxylation material, so that it is necessary to subdivide the latter in the workingup, are no longer acceptable. A further disadvantage of the known process is finally that the alkali metal salt of 2-hydroxydibenzofuran-3-carboxylic acid, which is perfectly desirable for further processing, cannot be isolated in substance from the very dilute aqueous solution without industrially unacceptable expense.

It is thus an object of the present invention to find a process which no longer has these disadvantages. This object is achieved with the present invention.

The invention thus provides a process for preparing 2-hydroxydibenzofuran-3-carboxylic acid, in particular in the form of its alkali metal salts, by reacting an alkali metal salt of 2-hydroxydibenzofuran with carbon dioxide at a temperature above 120° C., which comprises carrying out the reaction in an aliphatic alcohol having 4 to 8 carbon atoms. This reaction can be carried out without carbon dioxide pressure or under carbon dioxide pressure. Preferably the reaction is carried out under slight carbon dioxide pressure.

In this way the alkali metal salt of 2-hydroxydibenzofuran-3-carboxylic acid is obtained in high purity and high yield for example directly from its alcoholic suspension.

Solvents or diluents used according to the invention are in particular straight-chain or branched alkanols of 4 to 8 carbon atoms having a boiling point of above 100° C. Particular preference is given to hexanols and octanols, in particular 2-ethylhexanol. The aliphatic alcohols used according to the invention can be used alone or in mixture.

The alkali metal salts of 2-hydroxydibenzofuran which served as starting compounds are essentially the sodium and potassium salt, preferably the sodium salt. They can be prepared beforehand in a separate step in anhydrous form by known methods and then be introduced into the solvent or diluent used according to the invention. However, it is advantageous to integrate the preparation of the alkali metal salt in the process according to the invention by introducing the 2-hydroxydibenzofuran together with an alkali metal hydroxide, for example in the form of an aqueous alkali metal hydroxide solution, together into the solvent used according to the invention and removing the water therefrom by distillation. This distillation will in certain circumstances also remove some of the solvent, which however, can be easily replenished. Another method of preparing the alkali metal salt of 2-hydroxydibenzofuran comprises adding to the 2-hydroxydibenzofuran in a comparatively long-chain aliphatic alcohol, such as a hexanol or octanol, for example in 2-ethylhexanol, the solution of the requisite amount of an alkali metal alcoholate of a preferably lower aliphatic alcohol in a preferably lower aliphatic alcohol, such as, for example, a solution of sodium methylate in methanol, and heating this mixture to distil off the lower alcohol and where appropriate some of the longer-chain alcohol.

The alkali metal salt of 2-hydroxydibenzofuran can be used in the carboxylation reaction together with an excess of alkali. In general the molar ratio of alkali metal hydroxide to 2-hydroxydibenzofuran as components of the alkali metal salt of 2-hydroxydibenzofuran is (0.9–1.5):1, preferably (0.98–1.3):1; in particular, this molar ratio is (1.0–1.1):1. The alkali metal salt of 2-hydroxydibenzofuran is generally used in the reaction batch according to the invention in a concentration between 5 and 50% by weight, preferably between 10 and 25% by weight, based on the solvent or diluent used according to the invention.

The carboxylation temperature is generally between 150° and 240° C. Preference is given to using a temperature between 180° and 230° C., in particular between 215° and 225° C. If the reaction is carried out under carbon dioxide pressure, said pressure can vary within wide ranges. It is generally between 0.5 and 50 bar, preferably between 2 and 10 bar, in particular between 3 and 6 bar. If the reaction is carried out in the absence of carbon dioxide pressure, then this variant is practiced in particular when using a high-boiling alkanol. However, preference is given to working under a certain small carbon dioxide overpressure. The carbon dioxide required for the reaction can be introduced into the reaction batch for example by passing the carbon dioxide gas into the alcoholic suspension of the alkali metal salt of 2-hydroxydibenzofuran or by passing the carbon dioxide gas over this alcoholic suspension.

The carboxylation batch can be worked up on completion of the carboxylation reaction in conventional manner. For instance, the resulting alkali metal salt of 2-hydroxydibenzofuran-3-carboxylic acid can be simply isolated from the suspension of the solvent or diluent used in the process at room temperature or at elevated temperature, for example by filtration or centrifuging. It is also possible first to distil off most or all of the solvent used in the process and to suspend the left-behind alkali metal salt of 2-hydroxydibenzofuran-3-carboxylic acid in water and then to isolate it from the aqueous organic or aqueous suspension in conventional manner. A further way of isolating the alkali metal salt of 2-hydroxydibenzofuran-3-carboxylic acid comprises in the case where a sufficiently steam-volatile solvent or diluent is used in the carboxylation reaction distilling off this volatile solvent with steam and isolating the desired alkali metal salt from the aqueous suspension left behind.

To obtain 2-hydroxydibenzofuran-3-carboxylic acid itself, the suspension of the alkali metal salt can be acidified in conventional manner, for example with mineral acids, such as hydrochloric or sulfuric acid, and their freed 2-hydroxydibenzofuran-3-carboxylic acid can be isolated from the acid suspension by filtration or centrifuging.

The process according to the invention for carrying out the carboxylation reaction, including the possibly integrated proceeding salt formation of the 2-hydroxydibenzofuran and the dehydration of the reaction batch, can be carried out in conventional industrial apparatus, for instance in a sealable vessel (autoclave) which is equipped with a stirrer and which may be equipped with a simple distillation apparatus and receiver and which can if desired also be operated under higher pressures.

A preferred embodiment of the process according to the invention can be described for example as follows: to convert the 2-hydroxydibenzofuran into the alkali metal salt which is to serve as starting compound, first a solution or suspension of the 2-hydroxydibenzofuran in an alkanol of 4 to 8 carbon atoms having a boiling point of above 100° C. is heated together with the equivalent amount of an aqueous alkali metal hydroxide solution, such as an aqueous solution of sodium hydroxide or potassium hydroxide, at a temperature of above 100° C. with rising temperature until no water or no alcohol/water mixture distils over any longer. Any alcohol distilled off is subsequently replaced, insofar as is necessary. This alkali metal salt formation and removal of water is generally carried out under a nitrogen atmosphere. The solvent or diluent used is preferably an octanol, in particular 2-ethylhexanol. This salt formation is followed by the carboxylation reaction when carbon dioxide gas is introduced into and compressed in a sealed apparatus holding the suspension of the alkali metal salt of 2-hydroxydibenzofuran in the solvent or diluent used according to the invention. Preferably a $CO_2$ pressure of 3 to 6 bar is chosen. The temperature of the reaction batch is raised to 180 to 240, preerably to 215° to 225° C., and the carboxylation reaction is continued and completed within this temperature and $CO_2$ pressure range in the course of a number of hours. In general a reaction time of 3 to 6 hours is adequate. Thereafter the reaction batch is cooled down to about 80° to 100° C., and the resulting alkali metal salt of 2-hydroxydibenzofuran-3-carboxylic acid is isolated, for example by filtration.

The filtrate itself can be repeatedly reused in subsequent batches.

The examples below serve to illustrate the subject-matter of the invention in more detail. Parts and percentages are by weight, unless otherwise stated.

EXAMPLE 1

A mixture comprising 184 parts of 2-hydroxydibenzofuran, 1300 parts of 2-ethylhexanol and 180 parts of a methanolic solution containing 30% of sodium methylate is heated in a stirred autoclave to distil off the methanol at standard pressure; toward the end of the distillation the internal temperature is raised to the boiling point of 2-ethylhexanol, and about 200 parts of 2-ethylhexanol are distilled off. The resulting suspension of the sodium salt of 2-hydroxydibenzofuran in 2-ethylhexanol is then heated to 220° C. in the sealed autoclave and 4 bar of carbon dioxide are forced in. The carboxylation reaction is continued with stirring for 4 hours by maintaining the $CO_2$ pressure of 4 bar and the reaction temperature of 220° C. The batch is then cooled down to about 100° C., the product is filtered off with suction, and the filter residue is washed with ethanol and dried at 60° C.

This gives 198 parts of the sodium salt of 2-hydroxydibenzofuran-3-carboxylate having a purity of 94%, which corresponds to a yield of 74.5% of theory (the product contains about 6% of sodium carbonate).

The filtrate obtained form the carboxylation reaction on separation from the synthesis product is evaporated together with the ethanolic wash liquid to dryness under reduced pressure. The residue is taken up in water, and the solution is clarified with a little active carbon or kieselguhr and is then brought to a pH value between 7.0 and 6.8 with mineral acid, such as hydrochloric acid. This leads to the precipitation of about 32.5 parts of unreacted 2-hydroxydibenzofuran, which can be reused in a subsequent batch.

The yield of 2-hydroxydibenzofuran-3-carboxylic acid, based on reacted 2-hydroxydibenzofuran, is thus 90.5%.

EXAMPLE 2

In a stirred autoclave, a mixture of 184 parts of 2-hydroxydibenzofuran, 129 parts of 48% strength aqueous potassium hydroxide solution and 1300 parts of 2-ethylhexanol is constantly heated to above 110° C. with nitrogen passing over to distil off all the water. On reaching a boiling point of about 184° C., 200 parts of 2-ethylhexanol are additionally distilled off, and the batch is then heated in a sealed autoclave to 220° C. with introduction of carbon dioxide up to a pressure of 3 bar. The carboxylation reaction is continued for a further 4 hours while this $CO_2$ pressure and the reaction temperature are maintained. On cooling down of the carboxylation batch to about 100° C., the reaction product is filtered off with suction, and the filter residue is washed with ethanol and dried at about 60° C.

This gives 209 parts of the potassium salt of 2-hydroxydibenzofuran-3-carboxylic acid having a purity of 92%, which corresponds to a yield of pure product of 72.1% of theory (the product contains about 8% of potassium carbonate).

The unreacted 2-hydroxydibenzofuran remaining in the filtrate can be recovered in accordance with the directions of Example 1.

The yield of 2-hydroxydibenzofuran-3-carboxylic acid, based on reacted 2-hydroxydibenzofuran, is thus 87.6%

EXAMPLE 3

To prepare the sodium salt of 2-hydroxydibenzofuran-3-carboxylic acid the procedure of Example 1 is followed, except that the reaction is carried out under a carbon diozide pressure of 6 bar, affording the desired end product in the yield and purity indicated in Example 1.

EXAMPLE 4

To prepare the sodium salt of 2-hydroxydibenzofuran-3-carboxylic acid the procedure of Example 1 is followed, except that the indicated amount of 2-ethylhexanol is replaced by the untreated filtrate without the ethanolic wash liquid from previous batches in the same amount, merely adding, because the filtrate contains 2-hydroxydibenzofuran or the sodium salt thereof, 151.5 parts of 2-hydroxydibenzofuran and the equivalent amount of 148 parts of a methanolic solution containing 30% of sodium methylate.

This gives 197 parts of the desired sodium salt of 2-hydroxydibenzofuran-3-carboxylic acid having a purity of 94%.

Here, too, the filtrate can again be used in a subsequent batch.

We claim:

1. A process for the preparation of 2-hydroxy-dibenzofuran-3-carboxylic acid in the form of its alkali metal salt, consisting essentially of:
    reacting the alkali metal salt of 2-hydroxy-dibenzofuran with carbon dioxide at a temperature above 120° C. in an alkanol of 4 to 8 carbon atoms.

2. The process according to claim 1, which comprises:
    heating 2-hydroxy-dibenzofuran with an equivalent amount or an excess of either, aqueous alkali or alkali metal alcoholate, in an alkanol of 4 to 8 carbon atoms while distilling off water in the first case or distilling off the alcohol corresponding to the alkali metal alcoholate in the second case and, subsequently, without intermediate isolation of the alkali metal salt of 2-hydroxy-dibenzofuran thus formed, subjecting said alkali metal salt of 2-hydroxy-dibenzofuran in said alkanol to said reaction with carbon dioxide.

3. The process according to claim 1, wherein the reaction is carried out under carbon dioxide pressure.

4. The process according to claim 1, wherein said alkanol is an octanol.

5. The process according to claim 1, wherein said alkanol is 2-ethyl-hexanol.

6. The process according to claim 1, wherein said temperature is between 180° and 230° C.

7. The process according to claim 1, wherein said temperature is between 215° and 225° C.

8. The process according to claim 1, wherein said alkanol which has been used in the carboxylation batch, is used again without regeneration in a subsequent batch.

9. The process according to claim 1, wherein 2-hydroxy-dibenzofuran-3-carboxylic acid in the form of its alkali metal salt is isolated from the alkanol as the alkali metal salt.

10. The process according to claim 1, wherein, after the carboxylation reaction and the formation of 2-hydroxy-dibenzofuran-3-carboxylic acid in the form of its alkali metal salt, the alkali metal salt is converted to the corresponding carboxylic acid form and isolated as such.

11. A process for the preparation, in a reaction medium, of 2-hydroxy-dibenzofuran-3-carboxylic acid in the form of its alkali metal salt, said process comprising:
    reacting an alkali metal salt of 2-hydroxy-dibenzofuran with carbon dioxide at a temperature above 120° C. in a solvent or diluent, wherein said solvent or diluent consists essentially of an alkanol of 4 to 8 carbon atoms, and wherein the amount of alkali metal in the reaction medium is equal to or greater than the amount needed to provide the alkali metal salt of 2-hydroxy-dibenzofuran.

12. The process according to claim 11, wherein the reaction is carried out under carbon dioxide pressure.

13. The process according to claim 11, wherein said alkanol is an octanol.

14. The process according to claim 11, wherein said alkanol is 2-ethyl-hexanol.

15. The process according to claim 11, wherein said temperature is between 180° and 230° C.

16. The process according to claim 15, herein said temperature is between 215° and 225° C.

17. The process according to claim 11, wherein said alkanol, which has been used in the carboxylation batch, is used again without regeneration in a subsequent batch.

18. The process according to claim 11, wherein 2-hydroxy-dibenzofuran-3-carboxylic acid in the form of its alkali metal salt is isolated from the alkanol as the alkali metal salt.

19. The process according to claim 11, wherein, after the carboxylation reaction and the formation of 2-hydroxy-dibenzofuran-3-carboxylic acid in the form of its alkali metal salt, the alkali metal salt is converted to the corresponding carboxylic acid form and isolated as such.

20. A process for the preparation of 2-hydroxy-dibenzofuran-3-carboxylic acid in the form of its alkali metal salt, comprising:
    heating 2-hydroxy-dibenzofuran with an equivalent amount or an excess of either aqueous alkali or alkali metal alcoholate, in an alkanol of 4 to 8 carbon atoms, while distilling off water in the first case or distilling off the alcohol corresponding to the alkali metal alcoholate in the second case and, subsequently, without intermediate isolation of the resulting alkali metal salt of 2-hydroxy-dibenzofuran thus formed, subjecting said alkali metal salt of 2-hydroxy-dibenzofuran in said alkanol to reaction with carbon dioxide at a temperature above 120° C.

21. The process according to claim 20 wherein, after the reaction with carbon dioxide and the formation of 2-hydroxy-dibenzofuran-3-carboxylic acid in the form of its alkali metal salt, the alkali metal salt is converted to the corresponding carboxylic acid form and isolated as such.

* * * * *